(12) United States Patent
Funakoshi et al.

(10) Patent No.: US 8,691,355 B2
(45) Date of Patent: Apr. 8, 2014

(54) FILM DRESSING

(75) Inventors: Yoshio Funakoshi, Osaka (JP); Seishi Suzuki, Osaka (JP)

(73) Assignee: Nitto Denko Corporation, Ibaraki (JP)

( * ) Notice: Subject to any disclaimer, the term of this patent is extended or adjusted under 35 U.S.C. 154(b) by 284 days.

(21) Appl. No.: 13/124,490

(22) PCT Filed: Oct. 15, 2008

(86) PCT No.: PCT/JP2008/068655
§ 371 (c)(1),
(2), (4) Date: Jun. 10, 2011

(87) PCT Pub. No.: WO2010/044152
PCT Pub. Date: Apr. 22, 2010

(65) Prior Publication Data
US 2011/0229676 A1  Sep. 22, 2011

(51) Int. Cl.
*B32B 9/04* (2006.01)
*B32B 3/04* (2006.01)
*A61F 13/02* (2006.01)
*A61L 15/14* (2006.01)

(52) U.S. Cl.
USPC ........... 428/40.1; 428/41.7; 428/43; 428/121; 428/124; 602/41; 602/57; 602/60; 128/888; 128/889; 206/440; 206/441

(58) Field of Classification Search
USPC .......... 428/40.1, 41.7, 41.8, 43, 98, 121, 124, 428/126, 129; 602/41, 57, 60; 128/888; 128/889; 206/440, 441
See application file for complete search history.

(56) References Cited

U.S. PATENT DOCUMENTS
2008/0281246 A1   11/2008 Effing et al.

FOREIGN PATENT DOCUMENTS

| DE | 102005009634 A1 | 9/2006 |
| JP | 58-124123 U | 8/1983 |
| JP | 07-038138 U | 7/1995 |
| JP | 09-154872 A | 6/1997 |
| JP | 2003-339762 A | 12/2003 |
| JP | 3135535 U | 9/2007 |

OTHER PUBLICATIONS

Japanese Patent Office, Office Action in Japanese Patent Application No. 2007-110698 (Oct. 25, 2011).
The International Bureau of WIPO, International Preliminary Report on Patentability in International Application No. PCT/JP2008/068655 (May 17, 2011).
European Patent Office, Extended European Search Report in European Patent Application No. 08877410.4 (Feb. 1, 2013).
Japanese Patent Office, International Search Report in International Patent Application No. PCT/JP2008/068655 (Jan. 20, 2009).

*Primary Examiner* — Patricia L Nordmeyer
(74) *Attorney, Agent, or Firm* — Leydig, Voit & Mayer, Ltd.

(57) ABSTRACT

Disclosed is a film dressing comprising a film dressing body. The film dressing body (1) comprises a film (2) and a pressure-sensitive adhesive layer (3) provided on one side of the film (2). The film dressing further comprises a release liner (4) covering the pressure-sensitive adhesive layer (3) on its adhesive face, and a carrier (5) covering the backside of the film (2). A carrier division part (5*d*) is provided to divide the carrier (5) into a carrier first part (51) and a carrier second part (52). A flap layer (7) is stacked so as to cover the carrier division part (5*d*). A flap layer division part (7*d*) is provided in the flap layer (7) to divide the flap layer (7) into a flap layer first part (71) and a flap layer second part (72) which are partially joined respectively on the carrier first pat (51) and the carrier second part (52). Preferably, division parts (4*d*1, 4*d*2) are provided in the release liner (4).

8 Claims, 11 Drawing Sheets (a)

(b)

(c)

(a)

(b)

(c)

(d)

(e)

(a)

(b)

(c)

(d)

(e)

(a)

(b)

(a)

(b)

(c)

(d)

(e)

(a)

(b)

(a)

(b)

(a)

(b)

FILM DRESSING

TECHNICAL FIELD

The present invention relates to a film dressing for medical use or surgical use. More particularly, the present invention relates to a film dressing to be used, for example, for covering a wounded area, or fixing a medical device such as a catheter.

BACKGROUND ART

Being widely used to fix medical devices such as catheters, as a wound-covering material, and for other purposes, the film dressing is a kind of adhesive sheet comprising a film adaptive to the skin and an adhesive layer provided on one primary face of the film.

Any film dressing, while in the state before use (during the distribution stage and the like), normally assumes a multi-layer laminated structure comprising the aforementioned adhesive sheet and the following elements (a) and (b) added thereto.

(a) A release liner that covers the adhesive layer face (adhesive face).

(b) A carrier laminated as a separable support layer on the other primary face (back face) of the film (the carrier is to confer rigidity to the adhesive sheet so as to prevent the handlability of the adhesive sheet from worsening even with the removal of the release liner).

In applying a film dressing to the skin and the like, the release liner is first removed to expose the adhesive face of the adhesive layer, the film dressing is applied to the skin, (including fixation of a medical device such as a catheter or gauze), thereafter the carrier is separated to complete the operation of application.

However, when the present inventors extensively investigated the actual status of use of conventional film dressings, the problem shown below was revealed.

Since film dressings are used mainly in medical practice settings, the aforementioned series of steps of the operation of application is usually performed while wearing rubber gloves for medical use and the like. The aforementioned problem is a problem with a lack of the ease of carrier separation while wearing rubber gloves because of the absence of an adequate holding margin due to a thin carrier.

Over the above-described problem, in Patent Document 1, the carrier is divided at the central portion thereof (the dividing line is referred to as a "mutually butted part"), and the "mutually butted part" is further covered with a "support release piece", in an attempt to facilitate the operation of carrier separation.

However, with the configuration described in the publication, only one of the two divided sections of the carrier is separated by the "support release piece", whereas the other section of the carrier remains as it is, and is still difficult to separate.

Another embodiment is available wherein a holding margin or the like is formed on the outer periphery, without providing a dividing portion in the carrier, and the carrier is removed entirely from the margin. However, that embodiment does not pose a problem with regard to waterproofness and the like when a wounded area is simply covered with a film dressing, but when a catheter or the like is to be fixed, carrier rigidity can prevent sufficient fixation to pose major problems such as the drop of the catheter.

Meanwhile, taking note of release liner manipulability, because the operation of application is performed while wearing rubber gloves for medical use and the like, as in the above-described case of a carrier, the problem of poor manipulability (handlability) arises due to the attaching of the rubber gloves to the adhesive face exposed upon elimination of the release liner.

Patent Document 1: JP-A-2003-339762

DISCLOSURE OF THE INVENTION

Problems to Be Solved by the Invention

It is an object of the present invention to provide a film dressing that allows a wide variety of medical devices such as catheters to be fixed well onto body surfaces, while functioning well as a carrier for conferring rigidity to the film dressing, and that offers good manipulability during separation of the carrier.

It is another object of the present invention to provide a film dressing that improves release liner manipulability and offers improved workability for the series of application operations of exposing the adhesive face, applying the release liner thereto, and separating the carrier, while solving the above-described problem with carriers.

Means of Solving the Problems

The present inventors conducted extensive investigations to accomplish the objects, and found that any catheter and the like could be fixed well, and the operation of eliminating the carrier is facilitated, by providing a dividing portion in the carrier, further providing a flap layer that covers the dividing portion, and also providing a dividing portion in the flap layer, and have developed the present invention.

In addition, the present inventors arrived at developing a film dressing that secures a holding margin (grasping margin) for holding the entire film even with the release liner eliminated partially, and that offers good manipulability for both the faces on the carrier side and release liner side, by providing a dividing portion in the release liner.

Accordingly, the film dressing of the present invention has the features shown below.

A film dressing comprising: a film dressing body having a film and an adhesive layer provided on one face of the film;

a release liner covering an adhesive face of the adhesive layer and releasably laminated thereon; and a carrier covering the other face of the film and releasably laminated thereon, wherein the carrier has a carrier-dividing portion that divides the outer shape thereof, whereby the carrier is divided into a carrier first portion and a carrier second portion, a flap layer that covers the carrier-dividing portion is further laminated on the carrier, and the flap layer has a flap layer-dividing portion that divides an outer shape thereof, whereby the flap layer is divided into a flap layer first portion and a flap layer second portion, and a partial region of the flap layer first portion is joined to the carrier first portion so as to leave a holding margin, and a partial region of the flap layer second portion is joined to the carrier second portion so as to leave a holding margin.

In a preferred embodiment of the present invention, the carrier-dividing portion is linear, the carrier first portion and the carrier second portion are in contact with each other at the carrier-dividing portion, or the carrier-dividing portion is band-shaped, and the carrier first portion and the carrier second portion are apart from each other with the carrier-dividing portion sandwiched therebetween.

In another preferred embodiment of the present invention, the flap layer first portion is joined to the carrier first portion in a region abutting the carrier-dividing portion or in a region in the vicinity of the carrier-dividing portion, and the flap layer second portion is joined to the carrier second portion in a region abutting the carrier-dividing portion or in a region in the vicinity of the carrier-dividing portion.

In another preferred embodiment of the present invention, the carrier-dividing portion is band-shaped, and the carrier first portion and the carrier second portion are apart from each other with the carrier-dividing portion sandwiched therebetween, and
wherein, the band-shaped carrier-dividing portion, comprises a filling layer having approximately the same width and thickness as those of the carrier-dividing portion is, the filling layer releasably inserted from the other face of the film, the filling layer having a dividing portion along the orientation of the carrier-dividing portion, whereby the filling layer is divided into a filling layer first portion and a filling layer second portion, the flap layer first portion is bonded straddlingly to the filling layer first portion and the carrier first portion, and the flap layer second portion is bonded straddlingly to the filling layer second portion and the carrier second portion.

In another preferred embodiment of the present invention, the running direction of the flap layer-dividing portion is approximately the same as the running direction of the carrier-dividing portion.

In another preferred embodiment of the present invention, the flap layer is a layer made of a flexible film or a layer made of a flexible unwoven fabric.

In another preferred embodiment of the present invention, the release liner comprises one or more linear release liner-dividing portions that divide the outer shape of the release liner.

In another preferred embodiment of the present invention, the release liner comprises two release liner-dividing portions in which running directions thereof are approximately the same each other.

In another preferred embodiment of the present invention, the running direction of the release liner-dividing portion is approximately the same as the running direction of the carrier-dividing portion.

Effect of the Invention

In the film dressing according to the present invention (hereinafter also simply referred to as the dressing), the carrier is, firstly, divided by a dividing portion into a carrier first portion and a carrier second portion. Because is this allows the entire dressing to be easily foldable at the dividing portion, it is possible to preferably fix the catheter to the skin even if the catheter is elevated.

Next, in the present invention, a flap that covers the aforementioned carrier-dividing portion is provided, the flap being divided into two pieces which are joined to a carrier first portion and a carrier second portion, respectively, to yield a holding margin. This allows the two divided carriers to be separated easily by picking the flap, even while wearing rubber gloves for medical use.

In the present invention, in addition to the above-described improvement in the carrier, a dividing portion is further provided in the release liner further. Thereby, even after the release liner is partially removed, a holding margin remains in the dressing. Thereby, it is possible to apply the dressing to a body surface, without contacting the adhesive face, even while wearing rubber gloves for medical use.

In particular, by providing two dividing lines that run in the same direction as each other to divide the release liner into three portions, the release liner remains on both sides even after the central portion of the release liner is removed. Thereby, it is possible to hold the dressing securely by both hands, without contacting the adhesive face, thus further improving the manipulability of application. Hence, it is possible to smoothly perform sequential applicating operations of removing the release liner, applying the dressing to a body surface, and removing the carrier, while wearing rubber gloves.

| [Explanation of symbols] | |
| --- | --- |
| 1 | film dressing body |
| 2 | film |
| 3 | adhesive layer |
| 4 | release liner |
| 4d1 | release liner-dividing portion |
| 4d2 | release liner-dividing portion |
| 5 | carrier |
| 5d | carrier-dividing portion |
| 51 | carrier first portion |
| 52 | carrier second portion |
| 7 | flap layer |
| 7d | flap layer-dividing portion |
| 71 | flap layer first portion |
| 72 | flap layer second portion |

BEST MODE FOR CARRYING OUT THE INVENTION

Hereinafter, the present invention is described with reference to specific example embodiments.

Figure 1:
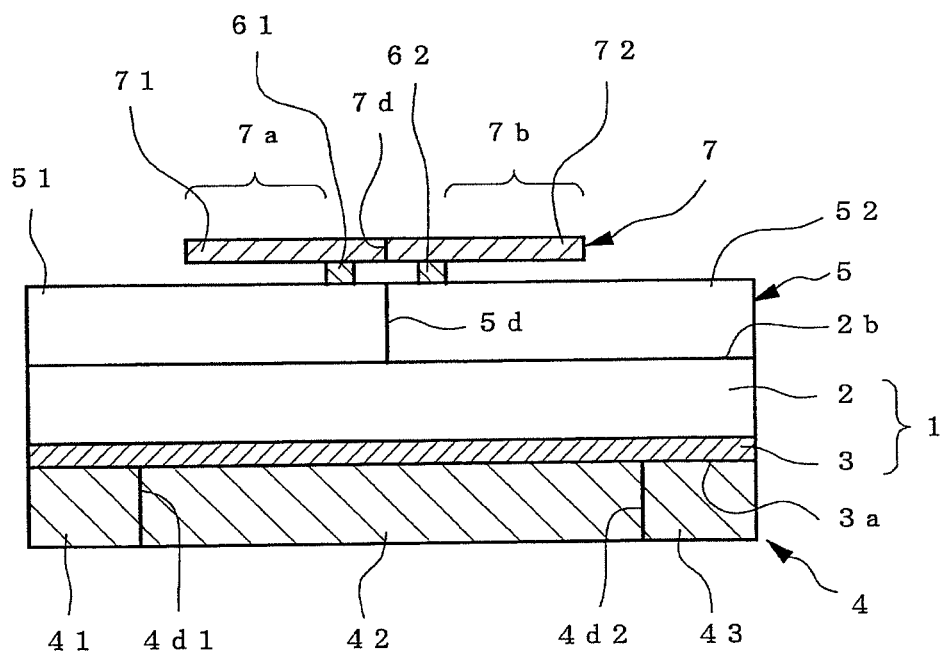
FIG. 1 is a side view that schematically illustrates a laminate structure of an example of the film dressing according to the present invention. In the figure, the hatching is added as appropriate to allow the individual layers to be easily distinguishable from each other. The same reason for the hatching applies to other drawings.

FIG. 1 is a side view that schematically shows a laminate structure of an example of the dressing. As illustrated in the figure, the dressing comprises a film dressing body 1 made of a film 2 having flexibility, and an adhesive layer 3 provided on one face of the film. The dressing further has a release liner 4 releasably laminated thereon covering the adhesive face 3a of the adhesive layer 3, and a carrier 5 releasably laminated on the other face 2b of the film 2 as a support layer.

The carrier 5 is provided with a carrier-dividing portion 5d that divides the outer shape thereof, whereby the carrier 5 is divided into a carrier first portion 51 and a carrier second portion 52.

A flap layer 7 is further laminated on the carrier 5 in a way such that it covers the carrier-dividing portion 5d. In FIG. 1, the bonding layers 61 and 62 are illustrated with greater thicknesses than they are for the sake of emphasis, so that the flap layer 7 appears to be widely apart from the carrier 5, but the actual bonding layers 61 and 62 are thin, the flap layer 7 being in contact with the carrier 5. The flap layer 7A has a flap layer-dividing portion 7d that divides the outside shape thereof, whereby the flap layer 7 is divided into a flap layer first portion 71 and a flap layer second portion 72.

Here, the flap layer first portion 71 is joined to the carrier first portion 51 in a partial region so as to leave a holding margin 7a, and the flap layer second portion 72 is joined to the carrier second portion 52 in a partial region so as to leave a holding margin 7b. Hence, the flap layer first portion 71 is partially joined to the carrier first portion 51 via the bonding layer 61, whereby the holding margin 7a is made to be in a cantilevered state by the bonding layer 61, representing an embodiment of a flap with a free end. The flap layer second portion 72 is likewise partially joined to the carrier second portion 52 via the bonding layer 62, whereby the holding margin 7b is made to be in a cantilevered state by the bonding layer 62, representing an embodiment of a flap having a free end.

The above-described configuration allows the dressing to be foldable at the carrier-dividing portion 5d to follow the elevation of the catheter, and to preferably fix the catheter, when covering a catheter in paracentesis, while being given rigidity by the carrier. After applying the dressing, it is possible to easily separate the carrier first portion 51 and the second portion 52 merely by pulling or stripping up the carrier portions while picking the holding margins 7a and 7b of the flap layer first portion 71 and the second portion 72, respectively.

The dressing may be a regular-sized product (cut product) or a long-sized product (rolled product).

The outer periphery shape and dimensions of the dressing are not subject to limitations. Referring to an example, when a regular-sized product is cut into a quadrangular shape such as a square or a rectangle, one having a width of 50 mm to 100 mm and a length of about 80 mm to 250 mm can be mentioned as a general purpose product. Outer periphery shapes of regular-sized products include not only quadrangles (corners may be rounded as appropriate), but also optionally chosen designs such as circles, oblongs, and irregulars. In case of a long-sized product, one having a belt width of about 50 mm to 150 mm is generally useful.

The dressing may be sterilized with radiations and the like, and may be packaged in separate sterile bags.

The film used as the substrate in the structure of the film dressing body may be one in use for conventionally publicly known film dressings, as far as it possesses flexibility and does not affect body surfaces such as the skin. Examples of materials useful for such films include polymers such as acrylic polymers, polyethylene, ethylene-vinyl acetate copolymers, polyurethane, polyether polyester and nylon derivatives. Thereof, polymers such as acrylic polymers, polyurethane, polyether polyester and nylon derivatives are particularly preferable, because they exhibit excellent water vapor permeability when prepared as films so that the breathing of the covered skin is not significantly interfered with, also because the skin whitening phenomenon can be suppressed, and still also because they can be applied while monitoring the application site (for example, while examining the catheter insertion portion in fixing a catheter in paracentesis) because the presence of transparency.

Although the thickness of the film is not limited, it is preferable, from the viewpoint of preferred functions for a film dressing, such as skin undulation followability, that the thickness be about 20 to 150 µm, more preferably 25 to 75 µm.

The material for the adhesive layer of the film dressing body may be an adhesive in use for publicly known adhesive sheets to be applied to body surfaces; examples include pressure-sensitive adhesives such as those of natural rubber series, synthetic rubber series, acrylic series, and silicone series. For further enhancing the transparency of the film, and further suppressing the irritation to the skin, an acrylic-series pressure-sensitive adhesive is preferably used.

Although the thickness of the adhesive layer is not limited, the thickness is normally preferably about 10 to 60 µm, particularly preferably about 20 to 50 µm.

As a method for providing an adhesive layer on one face of the film 2, a publicly known method may be used; examples include a method wherein an adhesive composition is coated and dried on a film, a method wherein an adhesive layer made of a previously molded adhesive composition is laminated on a film, and the like.

The carrier is a support layer for conferring rigidity to the film dressing body to improve the handlability. The carrier also serves as a protective layer that prevents the film from being flawed or broken before use, and that keeps the film surface in a sterile state for a long time when the dressing is sterilized.

Preferable materials for the carrier include plastic films (for example, polyethylene, polypropylene, polyester, and a complex of laminations thereof and the like), paper (for example, wood-free paper, craft paper and the like) and the like. Thereof, plastic films having transparency are particularly remarkably useful in fixing a medical device such as a catheter, because they can be applied while monitoring the application site through the dressing.

To releasably stick the carrier to the back face of the film, publicly known methods such as inflation molding, extrusion laminate molding, lamination molding, and casting can be used.

Although the thickness of the carrier varies depending on the material, it is normally preferably about 15 to 200 µm, more preferably about 20 to 100 µm.

The carrier-dividing portion does not always need to have completely cut the carrier at the beginning; an embodiment is acceptable wherein the carrier-dividing portion serves as the border to allow the carrier to be divided into a plurality of portions in separating the carrier.

For example, in the embodiment shown in FIG. 2(a), the carrier-dividing portion 5d has not completely divided the carrier, the notch entering the upper face of the carrier and staying on the midway. However, even in case of such incomplete division, the carrier can be separated into two divided portions at the carrier-dividing portion 5d, provided that the rest portion of the notch is thin and sufficiently brittle.

In the embodiment shown in FIG. 2(b), the carrier-dividing portion 5d has completely divided the carrier at the beginning, the notch entering the upper face of the carrier and reaching the lower face.

In these embodiments in FIGS. 2(a) and (b), when viewing the upper face of the carrier, the carrier first portion 51 and the carrier second portion 52 are in contact with each other at the carrier-dividing portion 5d, the carrier-dividing portion 5d appearing linear.

Meanwhile, in the embodiment in FIG. 2(c), the carrier-dividing portion 5d not only completely divides the carrier, but also separates the carrier first portion 51 and the carrier second portion 52 with a certain width 5w. Hence, when viewing the upper face of the carrier 5, the carrier-dividing portion 5d appears to be band-shaped with a width 5w.

An advantage of the linear carrier-dividing portion 5d resides in the ease of carrier separation, and in that the skin surfaces are more readily followable when fixing a catheter and the like.

Meanwhile, an advantage of the band-shaped carrier-dividing portion 5d resides in that the catheter fixability and followability further improve compared with the linear carrier-dividing portion.

The carrier-dividing portion may be not only in the above-described embodiments of linear and band-shaped carrier-dividing portions, but also in an embodiment wherein [although apparently notches and the like are absent, the texture of the portion is sufficiently brittle in terms of mechanical strength, and the brittle line acts as a dividing portion], and an embodiment wherein the portion is perforated, as well as an optionally chosen combination of these embodiments, and the like.

Figure 3:
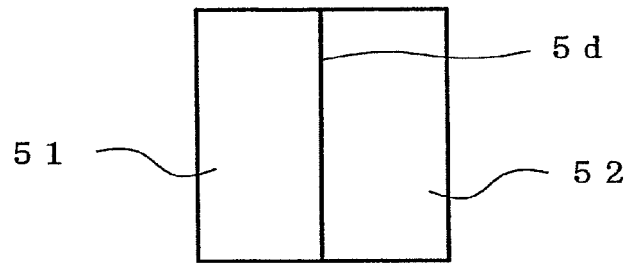
FIG. 3 shows views of example embodiments of the linear carrier-dividing portion in the present invention, wherein patterns drawn by the carrier-dividing portion are shown when viewing the upper face of the carrier.
Figure 3:
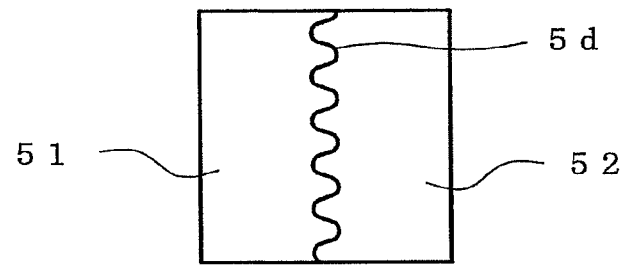
Figure 3:
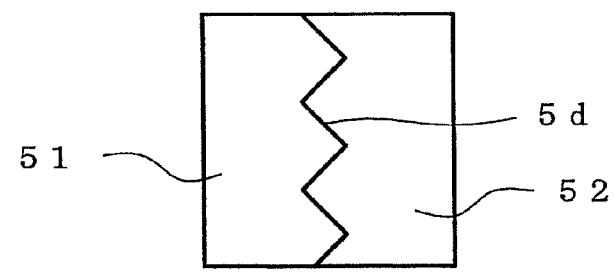
Figure 3:
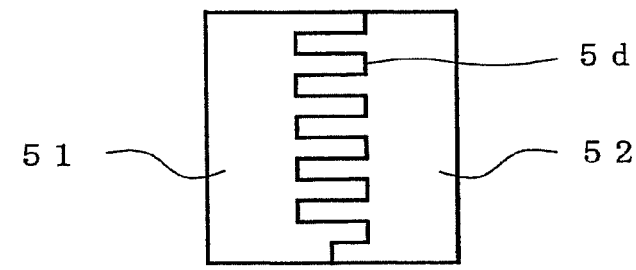
Figure 3:
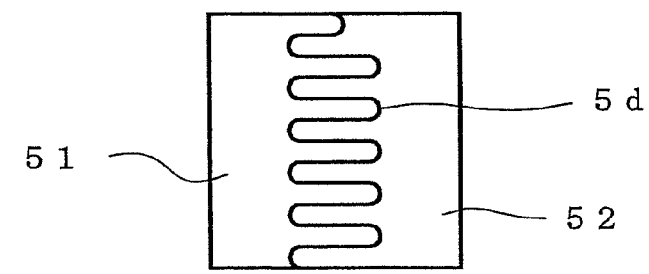
Figure 4:
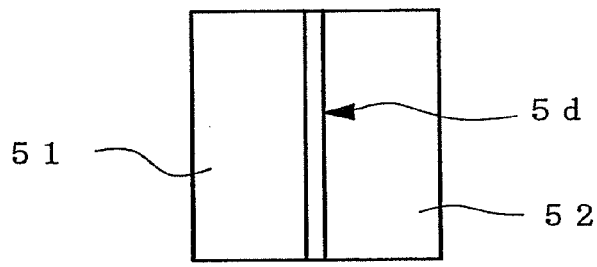
FIG. 4 shows views of example embodiments of the band-shaped carrier-dividing portion in the present invention, wherein patterns drawn by the carrier-dividing portion are shown when viewing the upper face of the carrier.
Figure 4:
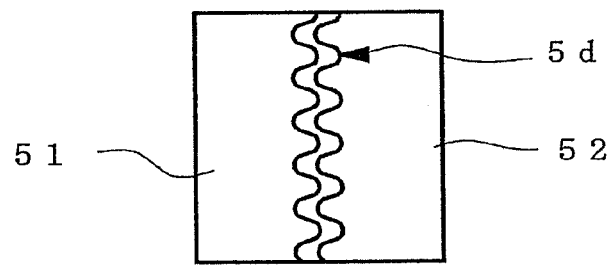
Figure 4:
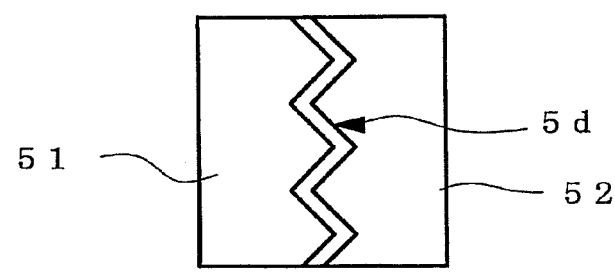
Figure 4:
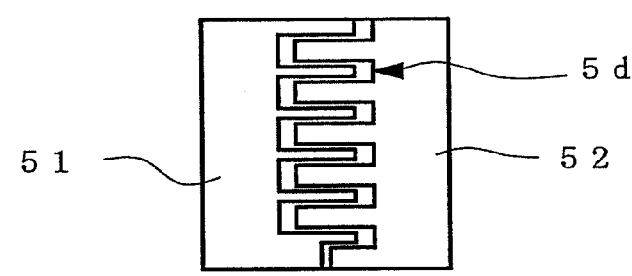
Figure 4:
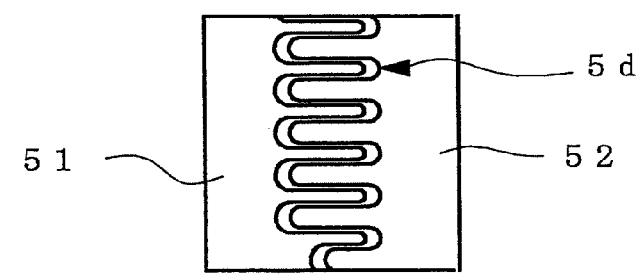

FIGS. 3 and 4 show views of example patterns drawn by the carrier-dividing portion when viewing the upper face of the carrier. The flap layer is not illustrated. FIG. 3 shows views of example cases where the carrier-dividing portion is linear. FIG. 4 shows views of example cases where the carrier-dividing portion is band-shaped, the carrier first portion 51 and the carrier second portion 52 being apart from each other with the band-shaped carrier-dividing portion 5d sandwiched therebetween, and the underlying film dressing body being exposed into the band-shaped carrier-dividing portion.

The pattern drawn by the carrier-dividing portion is preferably a pattern wherein the pattern starts at an optionally chosen site on the outer periphery of the carrier, passes the central portion of the carrier, and reaches the opposite side of the outer periphery of the carrier. In FIG. 3 and FIG. 4, in all examples, the carrier-dividing portion 5d approximately halves the entire rectangular dressing, from one side to the opposite side, into a carrier first portion 51 and a carrier second portion 52.

In FIG. 3(a) and FIG. 4(a), the carrier-dividing portion 5d is a simple straight line.

In FIG. 3(b) and FIG. 4(b), the carrier-dividing portion 5d is a wavy line such as a sine wave.

In FIG. 3(c) and FIG. 4(c), the carrier-dividing portion 5d is a wavy line such as a triangular wave or a sawtooth wave.

In FIG. 3(d) and FIG. 4(d), the carrier-dividing portion 5d is a wavy line such as a square wave.

In FIG. 3(e) and FIG. 4(e), the carrier-dividing portion 5d is a wavy line with great amplitude obtained by rendering the peak portion of a square wave semi-circular.

Regarding the pattern drawn by the carrier-dividing portion, a simple straight line offers good followability to partial elevations of the catheter and the like in fixing the catheter and the like, and a wavy line is advantageous in that the carrier is easily separable when being separated from the dividing portion.

The flap layer is a layer that gives a flap to the carrier that has been divided into two portions to serve as handles for separating the carrier first portion and the carrier second portion, respectively. For this reason, the flap layer is laminated covering the carrier-dividing portion, and is divided at the flap layer-dividing portion, only a part thereof is joined to the carrier, and the remaining portion forms a flap (free end).

The material for the flap layer is not particularly limited, and includes plastic films (for example, polyethylene, polypropylene, polyester, and a complex of laminations thereof and the like), paper (for example, wood-free paper, craft paper and the like), unwoven fabric and the like. Thereof, nearly transparent plastic films, paper with transparency and coarsely textured unwoven fabrics are remarkably useful in fixing a medical device such as a catheter, because they can be applied while monitoring the application site through the dressing.

The flap layer may be colored transparent to make it easier to distinguish the flap layer from other layers.

The flap layer may have a mechanical strength such that it does not become broken during the separating operation. A flexible flap layer without rigidity is preferable because the followability to the skin is excellent during the operation of fixing a catheter and the like.

Expressing preferable numerical values of the flexibility and rigidity of the flap layer, one having a loop hardness of 80 mN or less, particularly 15 to 60 mN, as determined by the loop compression method in accordance with JIS L1069, for example, is preferable.

The length from the flap layer-dividing portion to the outermost end face of the flap layer is not particularly limited; however, taking into account the portion that cannot serve as a flap due to the meandering width of the dividing portion and the presence of the adhesive layer and the like, as well as the adequate length of holding margin without a waste for a flap (about 5 mm to 15 mm), the length may be about 10 mm to 30 mm, more preferably in the range of 10 mm to 20 mm.

Although the thickness of the flap layer varies depending on the mechanical strength, elasticity, flexibility, and rigidity of the material, it is preferably about 10 to 200 μm, more preferably 20 to 150 μm, when the flap layer is foamed with, for example, a plastic film.

Figure 5:
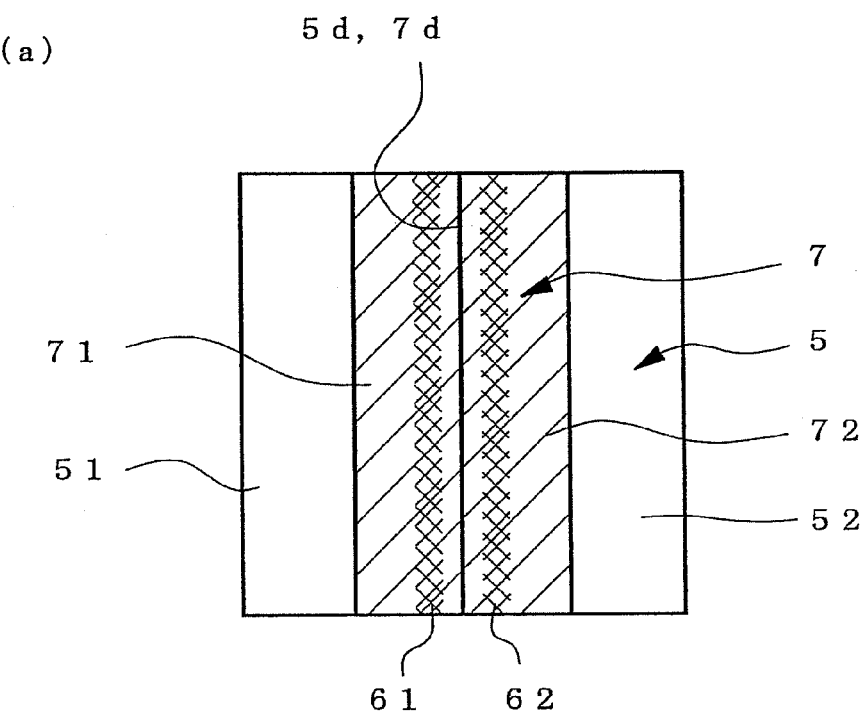
FIG. 5 shows views of how a flap layer works in using the film dressing according to the present invention.
Figure 5:
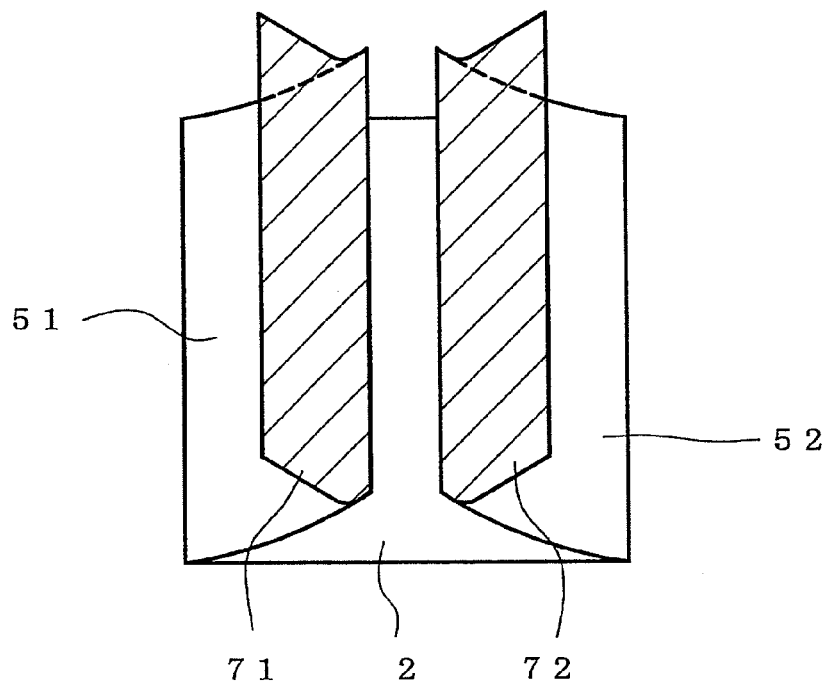
Figure 6:
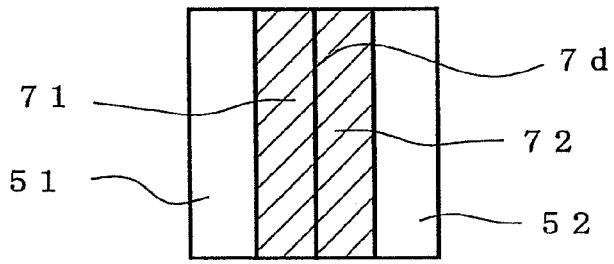
FIG. 6 shows views of example embodiments of the linear flap layer-dividing portion in the present invention, wherein patterns drawn by the carrier are shown when viewing the upper face of the flap.
Figure 6:
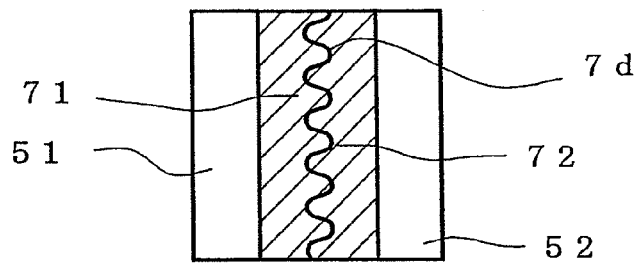
Figure 6:
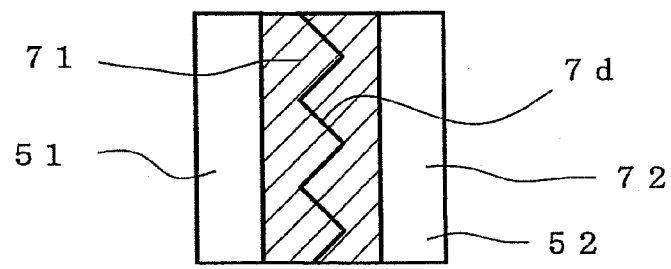
Figure 6:
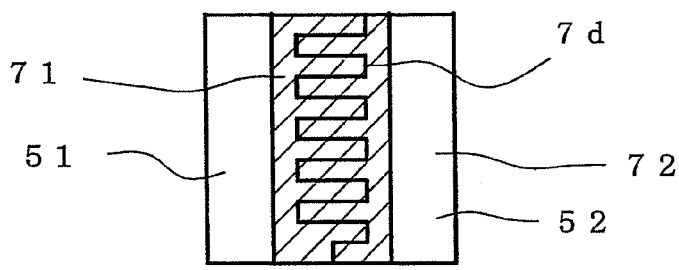
Figure 6:
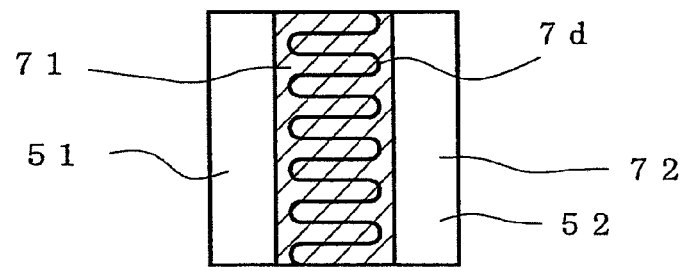

FIG. 5 shows views of how the flap layer works. To simplify the explanation, each of the lines of the carrier-dividing portion and the flap layer-dividing portion is drawn as a straight line; however, as illustrated in FIG. 6, the flap layer may be in an optionally chosen pattern.

As illustrated in FIG. 5(a), the flap layer 7 is laminated on the carrier 5 straddling the carrier-dividing portion 5d, and has a flap layer-dividing portion 7d provided therein, whereby the flap layer is divided into a flap layer first portion 71 and a flap layer second portion 72. In the example in the figure, the line of the carrier-dividing portion 5d and the line of the flap layer-dividing portion 7d coincide completely with each other.

The flap layer first portion 71 and the flap layer second portion 72 are partially bonded to the carrier first portion 51 and the carrier second portion 52 via underlying bonding layers 61 and 62, respectively. The bonding layers 61 and 62 are under the flap layer, and, in the figure, their positions are indicated with the dense hatching.

As illustrated in FIG. 5(a), in this example, the bonding layers 61 and 62 are provided on the side closer to the dividing portion, whereby each of the flap layer first portion 71 and the flap layer second portion 72 has a flap on the distal side away from the dividing portion, as illustrated in FIG. 5(b). FIG. 5(b) shows a state wherein this flap is being pulled in an attempt to remove the carrier.

As in the example in FIG. 5, an embodiment wherein the running direction of the flap layer-dividing portion 7d is approximately the same as the running direction of the carrier-dividing portion 5d (particularly, an embodiment wherein the patterns of both completely coincide with each other) is preferable in that the flap layer and the carrier can be removed together with a small force.

Here, the notion that the running directions of the two dividing portions are the same as each other includes two parallel lines, meaning that even when the two dividing portions are in a waving pattern, the directions in which they travel in the face are generally the same as each other. For example, provided that the two dividing portions draw respective sine waves, partially comparing the individual wavy lines, there are some cases where they cannot be said to be mutually parallel due to a phase discrepancy; however, if the two dividing portions run in similar directions as a whole, the running directions can be deemed the same as each other, and it can be judged that, as a whole, the two dividing portions exhibit the same action as two parallel lines.

Figure 2:
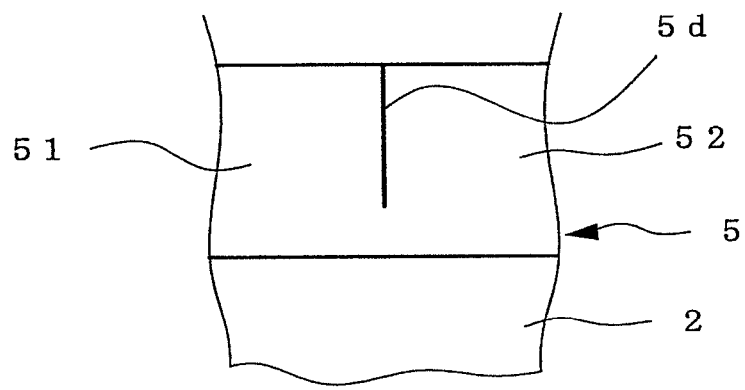
FIG. 2 shows side views of example embodiments of the carrier-dividing portion in the present invention.
Figure 2:
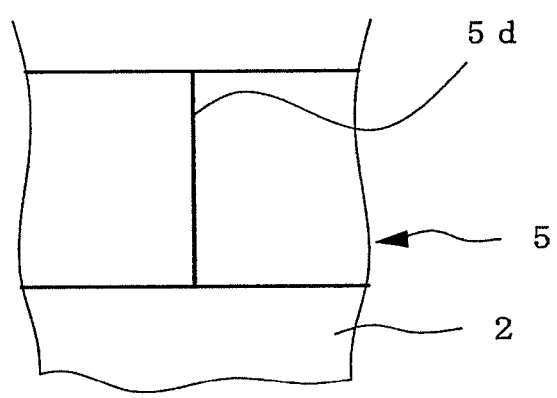
Figure 2:
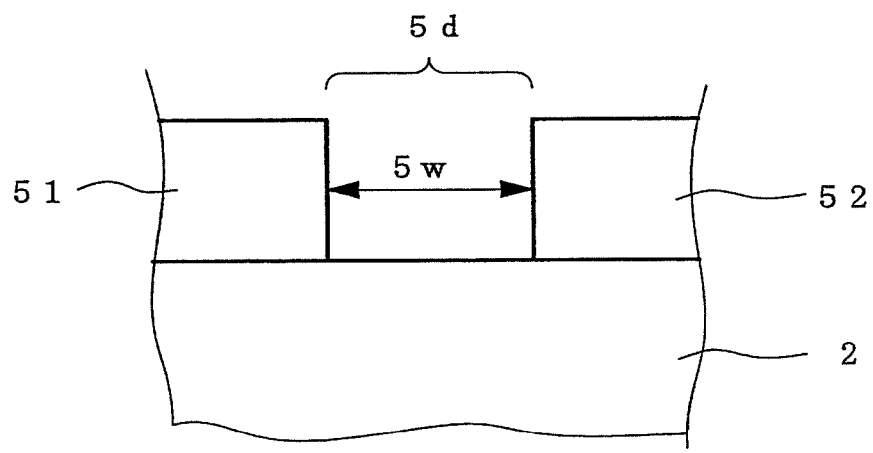

The flap layer-dividing portion, like the embodiment of the carrier-dividing portion shown in FIG. 2, does not always need to have completely cut the flap layer at the beginning; a half-cut embodiment wherein the notch enters the upper face of the flap layer and stays on the midway, an embodiment wherein the flap layer is completely divided, an embodiment wherein the flap layer is brittle along the line, an embodiment wherein the flap layer is perforated, and the like, as well as an embodiment comprising an optional combination thereof, and the like are acceptable, as far as they are embodiments wherein the flap layer-dividing portion serves as the border to allow the flap layer to be divided into a plurality of portions when pulling the flap portion to separate the carrier.

The pattern drawn by the flap layer-dividing portion can be the same pattern as the aforementioned carrier-dividing portion. Although the two portions may be in mutually different patterns, the flap layer and the carrier can be separated simultaneously with a small force when separating the flap layer, by making the pattern of the flap layer-dividing portion and the pattern of the carrier-dividing portion mutually agreeing overlapping patterns.

FIG. 6 shows views of the upper face of the flap layer, showing example patterns drawn by the flap layer-dividing portion. To make ti easy to distinguishing from the underlying carrier, the flap layer is hatched.

In FIG. 6(a), the flap layer-dividing portion 7d appears as a simple straight line.

In FIG. 6(b), the flap layer-dividing portion 7d appears as a wavy line such as a sine wave.

In FIG. 6(c), the flap layer-dividing portion 7d appears as a wavy line such as a triangular wave or a sawtooth wave.

In FIG. 6(d), the flap layer-dividing portion 7d appears as a wavy line such as a square wave.

In FIG. 6(e), the flap layer-dividing portion 7d appears as a wavy line with great amplitude obtained by rendering the peak portion of a square wave semi-circular.

The pattern of the flap layer-dividing portion is not subject to particular limitations; when the flap layer-dividing portion is wavy, with the provision that the amplitude of the wave is small over the entire external dimensions, as illustrated in FIG. 6(b), there is a feature that a holding margin is secured merely by folding the dividing portion with a small force when separating the flap layer. As illustrated in FIG. 6(e), with the provision that the amplitude of the wave is large, there is a feature that a sufficiently large holding margin is easy to obtain in the dividing portion when separating the carrier.

When the flap layer-dividing portion is made to assume a wavy pattern, the waveform, amplitude, and wavelength thereof may be freely chosen and combined according to the intended use.

Figure 7:
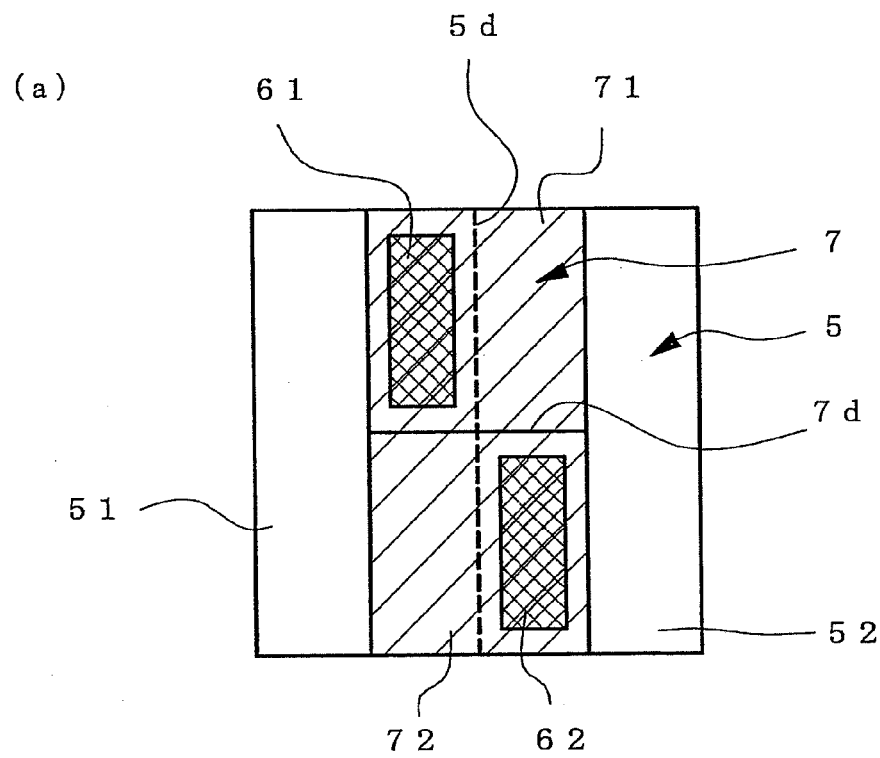
FIG. 7 shows views of other example patterns of the flap layer-dividing portion in the present invention.
Figure 7:
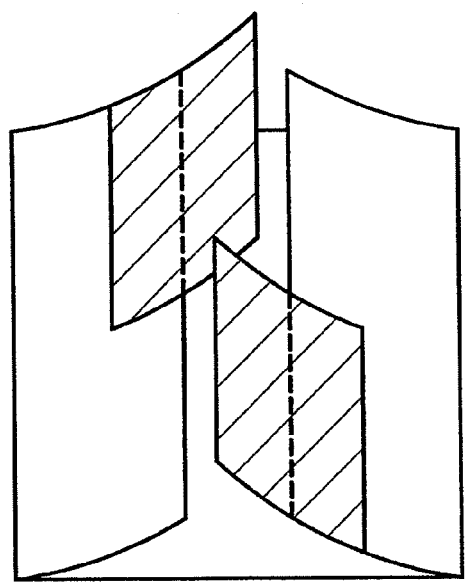

FIG. 7 shows views of other example patterns of the flap layer-dividing portion. In the example in the figure, the flap layer 7 is formed straddling the carrier-dividing portion 5d, which is indicated by the broken line, but the line of the flap layer-dividing portion 7d does not coincide with the line of the carrier-dividing portion 5d. However, because the flap layer first portion 71 and the flap layer second portion 72 are partially joined to the carrier first portion 51 and the carrier second portion 52, respectively, via underlying bonding layers (densely hatched portions) 61 and 62; therefore, a flap is formed also in the example in the figure. FIG. 7(b) shows a state wherein this flap is being pulled in attempt to remove the carrier.

As stated above, the flap layer first portion and the flap layer second portion may be as they are, as far as they are partially joined to the carrier first portion and the carrier second portion, respectively.

Figure 8:
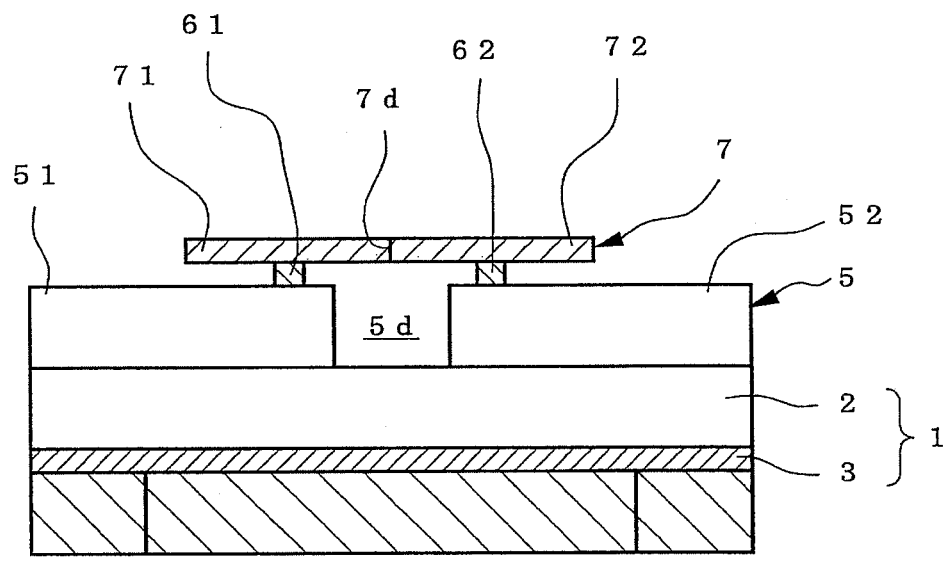
FIG. 8 shows side views of embodiments of a portion where the flap layer is picked in the present invention when the carrier-dividing portion is band-shaped.
Figure 8:
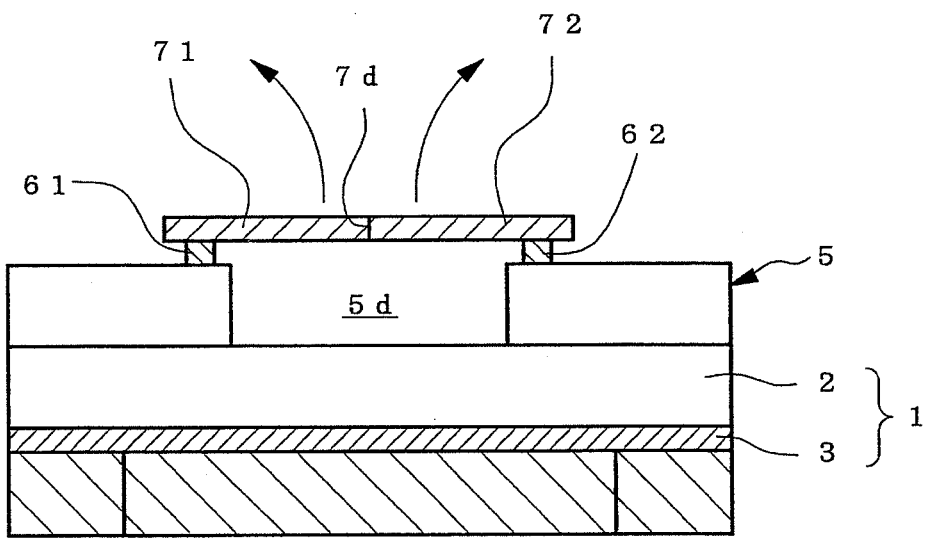

FIG. 8 shows side views of embodiments of a portion where the flap layer is picked (flap portion) when the carrier-dividing portion is band-shaped. The symbols for the various portions shown in the figure are the same as those in FIG. 1.

In the embodiment in FIG. 8(a), the carrier-dividing portion 5d is band-shaped, and the carrier first portion 51 and the carrier second portion 52 are apart from each other at a distance. The flap layer 7 is laminated covering the band-shaped carrier-dividing portion 5d, and the flap layer-dividing portion 7d is not band-shaped but linear, and covers and hides the carrier-dividing portion 5d. In this embodiment, the portion picked with fingertips as a flap forms the outside.

In contrast, in the embodiment in FIG. 8(b), the carrier-dividing portion 5d is band-shaped with a greater width than that in the embodiment in FIG. 8(a), so that the portion picked with fingertips as a flap forms the flap layer-dividing portion 7d side. Hence, as indicated by the arrows in the figure, the flap layer is opened at the center, and this is followed by separating the carrier.

As the bonding layer to bond the flap layer and the carrier, a known bonding material or adhesive can be used. It is also possible to use a material having a hot melt property as the bonding layer, and achieve bonding by heat sealing.

The bonding layer formation region may be continuous in belt-wise, or may be scattered. When the dividing portion draws a wavy line, the bonding layer may be formed in a way such that a wavy line will be drawn therealong, and may be formed in a straight belt in a slightly distant position. As in the latter case, an embodiment wherein a bonding layer is formed in a straight belt is preferable because the force required to separate the flap layer decreases.

When the bonding layer is band-shaped, the belt width thereof is preferably about 1 mm to 10 mm, depending on the size of the dressing.

Although the thickness of the bonding layer is not particularly limited, it is preferably in the range of about 30 μm to 200 μm.

An embodiment is preferable wherein a bonding layer is provided in a position close to the carrier-dividing portion, whereby, as shown in FIG. 5, the outside of the flap layer is used as a flap. By providing a bonding layer in a position close to the carrier-dividing portion, a force for elevating and removing the carrier from the carrier-dividing portion is exerted, so that the force required to achieve the separation decreases. If a bonding layer is provided in a position farther from the carrier-dividing portion, a greater force is required, and, occasionally, the film dressing body goes up from the skin. If the flap layer is pulled outwardly along the skin surface, the skin can be mechanically stimulated, so that an embodiment is preferable wherein the carrier is removed from the carrier-dividing portion as it is stripped up at a right angle to the skin surface.

Figure 9:
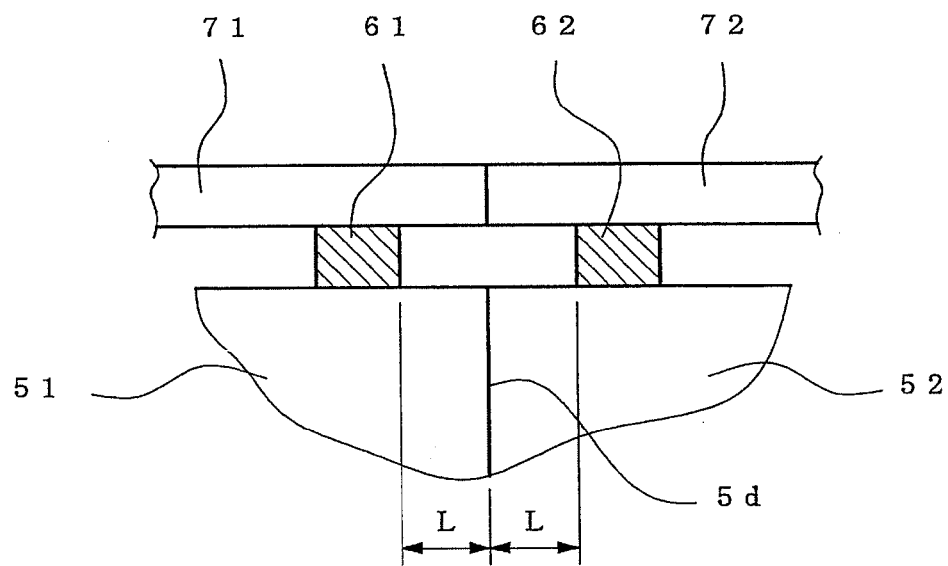
FIG. 9 shows preferable positions of a bonding layer immediately beneath a flap layer in the present invention.
Figure 9:
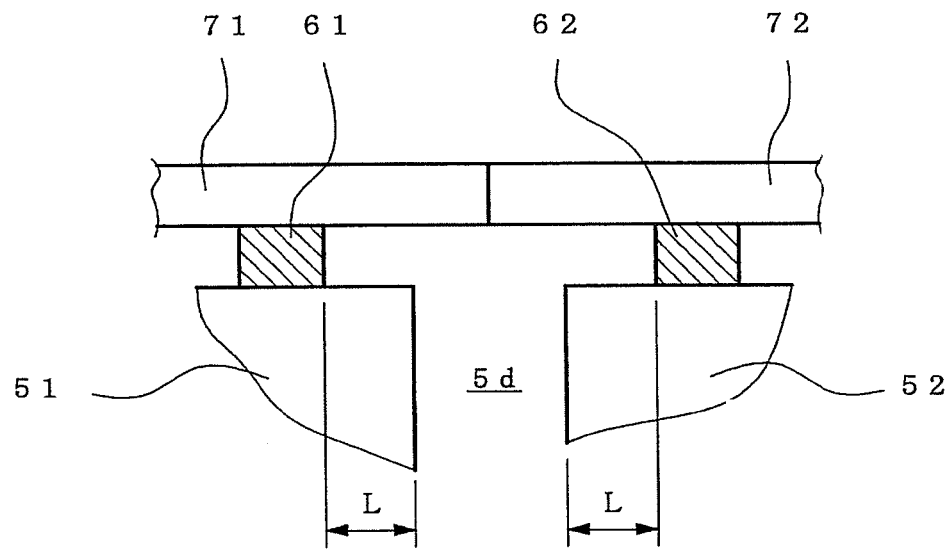

FIG. 9 shows preferable positions of a bonding layer. As shown in FIGS. 9(*a*) and (*b*), an embodiment is preferable wherein each of the bonding layers 61 and 62 is provided at a particular distance L from the end face of the carrier-dividing portion 5*d*.

Depending on the size of the dressing, the value of the distance L is preferably about 0 mm to 5 mm, and 0.5 mm to 3 mm is a more preferable distance. When the distance L is 0 mm, bonding material components can penetrate the carrier-dividing portion 5*d* and bond the carrier and the dressing; therefore, it is recommended that the distance be set at 0<L. If the distance L is greater than the upper limit 5 mm, the force required for the carrier to be separated from the film increases when the flap layer and the carrier are removed together, which in turn leads to the fear that the film dressing can detach itself from the skin surface or undergo an elevation, and to possible problems, including the flap layer detaching from the carrier and the like.

Figure 10:
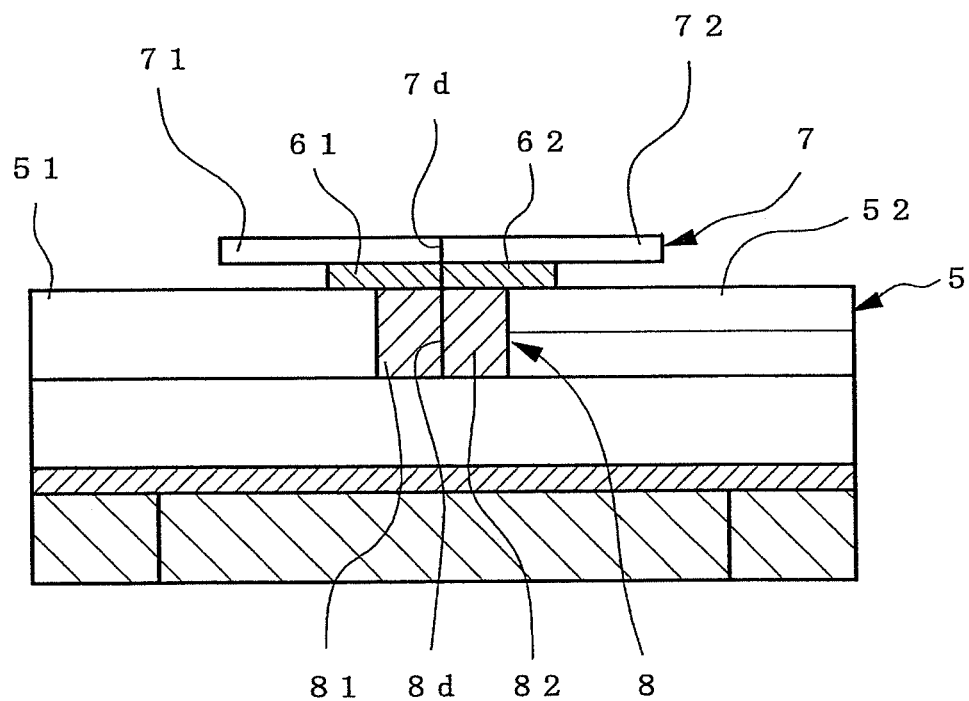
FIG. 10 is a side view showing a special embodiment of a flap layer in the present invention when the carrier-dividing portion is band-shaped.

FIG. 10 is a side view showing a special embodiment of a flap layer wherein the carrier-dividing portion is band-shaped. In the embodiment in the figure, a filling layer 8 having approximately the same width and thickness as those of the band-shaped carrier-dividing portion is inserted into the carrier-dividing portion. The filling layer 8, like the carrier, can be separated from the back face of the film 2.

Provided in the filling layer 8 is a dividing portion 8*d* along the running direction of the carrier-dividing portion (in the figure, perpendicular to the page plane), whereby the filling layer 8 is divided into a filling layer first portion 81 and a filling layer second portion 82. A flap layer 7 is provided to cover the filling layer, a flap layer first portion 71 (i.e., bonding layer 61) being bonded straddlingly to the filling layer first portion 81 and the carrier first portion 51, and a flap layer second portion 72 (i.e., bonding layer 62) being joined straddling the filling layer second portion 82 and the carrier second portion 52.

As the material for the filling layer, a material of low elasticity possessing appropriate rigidity, such as a plastic film or paper, can be used.

Examples of the manufacturing method for providing a filling layer as illustrated in FIG. 10 include publicly known methods of layer lamination, for example, the use of a bonding material, hot melting and the like.

The release liner used may be a conventionally publicly known one. Examples of the substrate portion of the release liner include plastic films (for example, polyethylene, polypropylene, polyester, or a complex of laminations thereof and the like), paper (for example, wood-free paper, craft paper and the like) and the like. By subjecting one primary face of this substrate portion to a silicone-series resin treatment, a fluorine-series resin treatment or the like for enabling the separation from the adhesive layer, a release liner can be obtained.

Although the thickness of the release liner is not limited, the thickness is normally preferably about 50 to 250 μm, more preferably about 75 to 200 μm.

By providing in the release liner one or more linear release liner-dividing portions that divide the outer shape thereof, the other release liner remains even after removing one release liner, so that the operation of application is possible without contacting the adhesive face, and the workability improves.

A preferred embodiment of the release liner-dividing portion is an embodiment wherein two portions whose running directions are approximately the same are provided. Hence, when the dividing portion is a straight line, an embodiment is preferable wherein two parallel release liner-dividing portions are provided. The advantages thereof are as described in the Effect of the Invention.

Figure 11:
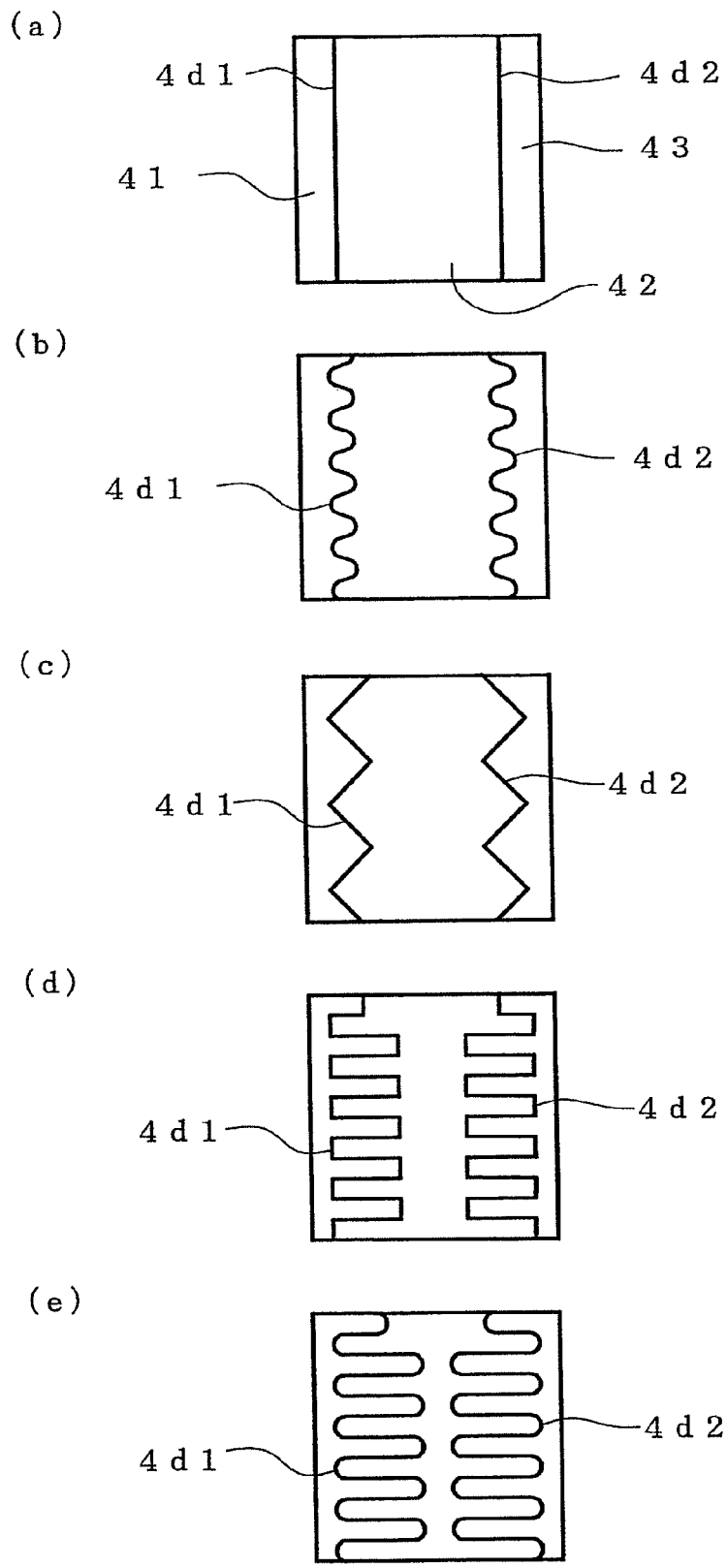
FIG. 11 shows example patterns drawn by the release liner-dividing portion in the present invention when viewing the release liner face.

FIG. 11 shows example patterns drawn by the release liner-dividing portion when viewing the release liner face. The examples in the figure are examples of cases where two release liner-dividing portions whose running directions are approximately the same as each other are provided.

The release liner-dividing portions 4*d*1 and 4*d*2 in the figure appear as simple straight lines in FIG. 11(*a*), as wavy lines such as sine waves in FIG. 11(*b*), as wavy lines such as triangular waves and sawtooth waves in FIG. 11(*c*), as wavy lines such as square waves in FIG. 11(*d*), and as wavy lines with great amplitude obtained by rendering the peak portion of the square wave semi-circular in FIG. 11(*e*).

Regarding the position of the release liner-dividing portion, when only one dividing portion is present, it is formed in a way such that it will divide the release liner in a position 10 mm or more apart from the side of an end of the release liner (=end of the film dressing body), preferably at the central portion. In cases where two release liner-dividing portions are present (including cases where more than one is further added), it is preferable from the viewpoint of securing a holding margin that the two portions be provided in positions 10 mm or more apart from the two opposite end sides on the outer periphery of the release liner, respectively.

EXAMPLES

Example 1

(Film Dressing Body)

A adhesive layer consisting of an acrylic-series adhesive was provided on a film 30 μm thick made of polyurethane to obtain a thickness of 30 μm, and this was used as the film dressing body.

(Release liner)

A release liner consisting of paper 100 thick whose surface has been treated with silicone resin was bonded to the adhesive face of the aforementioned adhesive layer.

(Carrier)

As a carrier, a film 40 μm thick made of biaxial oriented polypropylene (OPP) was releasably applied onto the back face of the film dressing body by extrusion laminate molding.

The central portion of the carrier had a linear notch line added thereto in a way such that the carrier would be completely divided, as shown in FIG. 2(*b*), and this was used as the carrier-dividing portion. Formation of the carrier-dividing portion was achieved using a die cut roll.

(Flap Layer)

A flap layer 40 μm thick and 50 mm wide made of an unwoven fabric was laminated covering the carrier-dividing portion. Formed in the flap layer was a flap layer-dividing portion in a pattern coinciding with the pattern of the carrier-dividing portion. The flap layer-dividing portion was achieved using a die cut roll.

Formed by halving the flap layer, a flap layer first portion and a flap layer second portion were bonded to a carrier first portion and a carrier second portion, respectively. The bonding material used was a styrene-isoprene-styrene-series hot melt bonding material.

The distance from the carrier-dividing portion to the bonding portion was set at 2 mm.

(Release Liner-Dividing Portion)

Having the outer shape of the film dressing as a square 100 mm×100 mm on sides, a straight dividing portion (notch) parallel to two mutually opposite sides was made in the release liner at 15 mm from each of the two sides, and this was used as the film dressing. The running directions of the carrier-dividing portion and the release liner-dividing portion were the same.

(Evaluation)

Gauze folded to a thickness of 2 mm was arranged on the skin, and the manipulability and fixability during fixation of the gauze covered with the dressing to the skin were evaluated.

First, even after the release liner of the central portion was eliminated, the release liner remained at both ends; therefore, it was possible to easily fix the gauze with the remaining release liners as holding margins, even while wearing rubber gloves.

In addition, after the film dressing was applied to the skin, each of the flaps outside of the two flap layers was pulled, whereby the carrier could be applied easily and cleanly without removal from the skin.

The fixation state of the gauze was good.

Example 2

In this example, a film dressing was prepared in the same manner as the example above except that the flap layer was formed with an OPP film 30 μm thick, and that the distance from the carrier-dividing portion to the bonding portion was set at 4 mm.

The manipulability and fixability were good as in Example 1 above.

Example 3

In this example, a film dressing was prepared in the same manner as Example 2 above except that the linear carrier-dividing portion was replaced with a band-shaped carrier-dividing portion, width of 10 mm, extending in a straight line, that the distance from the end of the band-shaped carrier-dividing portion to the bonding portion was set at 4 mm, and that only one release liner-dividing line was present on either side.

The manipulability and fixability were good as in Example 2 above.

Example 4

In this example, a dressing was prepared in the same manner as Example 3 above except that the carrier-dividing portion was a band-shaped carrier-dividing portion, width of 20 mm, that the distance from the end of the band-shaped carrier-dividing portion to the bonding portion was set at 2 mm, and that the dividing portions of the two release liners were present as in Example 1.

The manipulability and fixability were good as in Example 3 above.

Example 5

In this example, as shown in FIG. 10, the carrier-dividing portion was a 15 mm-wide band-shaped carrier-dividing portion, a film made of polyester, width 15 mm, thickness 38 μm, was inserted into the band-shaped carrier-dividing portion as a filling layer, over which a flap layer made of an OPP film was laminated. The filling layer had a dividing portion provided therein along the orientation of the carrier-dividing portion, and the filling layer was divided into a filling layer first portion and a filling layer second portion. Then, a dressing was prepared in the same manner as Example 4 above except that the flap layer first portion was bonded straddlingly to the filling layer first portion and a carrier first portion, and that the flap layer second portion was is bonded straddlingly to the filling layer second portion and a carrier second portion.

The manipulability and fixability were good as in Example 4 above.

Experiment 1

In this experiment, a film dressing was prepared in the same manner as Example 1 except that in search of a preferable value of the distance from the carrier-dividing portion to the bonding portion (distance L in FIG. 9($a$)), the distance was set at L=6 mm.

As a result, the operations from the elimination of the release liner to the application were good as in Example 1. However, regarding the separation of the carrier after application, because a wide distance from the carrier-dividing portion to the bonding portion was secured, the most preferable operating status wherein the carrier is sequentially stripped up from the dividing portion at a right angle to the skin surface was not achieved; a major force in the direction along the carrier face was exerted, whereby a force was also transmitted to the film dressing body, resulting in the dressing body being detached somewhat from gauze and the skin.

This experiment revealed that if the distance from the carrier-dividing portion to the bonding portion is too large, the carrier separability is no longer good even with the product of the present invention.

Regarding the relationship between the distance L from the carrier-dividing portion to the bonding portion and the separation manipulability of the carrier, the separation manipulability was good in Example 1 (distance L=2 mm) and not good in Experiment 1 (distance L=6 mm), so that a supplementary experiment for finding the range in detail was performed.

As a result, in case of L=0 mm, the carrier could be separated, but the phenomenon occurred in which the bonding material invaded the film dressing face from the carrier-dividing portion; in case of 1 mm≤L≤3 mm, the carrier could be particularly preferably separated; in case of 3 mm<L≤5 mm, some faults occurred; when the L value exceeded 5 mm, it became difficult to separate the carrier.

Experiment 2

In this experiment, a film dressing was prepared in the same manner as Example 1 except that the distance L from the carrier-dividing portion to the bonding portion was set at 6 mm, that a flap layer was formed with a film made of OPP, and that only one release liner-dividing portion was present on either side.

As a result, as in Experiment 1 above, the operations from the removal of the release liner to the application thereof was good, but the operation of separating the carrier after application was difficult.

Comparative Example 1

In this comparative example, a film dressing was prepared in the same manner as Example 1 except that no flap layer was provided, and that only one release liner-dividing line was present.

As a result, because one dividing portion was provided in the release liner, it was possible to easily fix gauze while wearing rubber gloves, as in Example 3, but the operation of eliminating the carrier was difficult due to the absence of a holding margin in the carrier.

Comparative Example 2

In this comparative example, a film dressing was prepared in the same manner as Example 3 except that no flap layer was provided.

As a result, because one dividing portion was provided in the release liner, it was possible to easily fix gauze even while wearing rubber gloves, as in Example 3, but the operation of eliminating the carrier was difficult due to the absence of a holding margin in the carrier.

Comparative Example 3

In this comparative example, a film dressing was prepared in the same manner as Example 4 except that the width of the band-shaped carrier-dividing portion was set at 10 mm, and that no dividing portion was formed in the release liner.

As a result, it was necessary to remove the release liner entirely; while wearing rubber gloves, the adhesive face came into contact with the rubber gloves and the manipulability was poor.

Because the width of the band-shaped carrier-dividing portion was set at 10 mm, the operation of removing the carrier was good.

The evaluation results in Examples 1 to 5 and the evaluation results in Comparative Examples 1 to 3, described above, are summarized in Table 1 below. Regarding release liner manipulability and carrier separation manipulability, a favorable rating is indicated with ○, and a poor rating with x.

TABLE 1

|  | Release liner manipulability | Carrier manipulability |
| --- | --- | --- |
| Example 1 | ○ | ○ |
| Example 2 | ○ | ○ |
| Example 3 | ○ | ○ |
| Example 4 | ○ | ○ |
| Example 5 | ○ | ○ |
| Comparative Example 1 | ○ | X |
| Comparative Example 2 | ○ | X |
| Comparative Example 3 | X | ○ |

As is evident from the results in Table 1 above, the film dressing according to the present invention was found to be good in terms of carrier separation manipulability and manipulability concerning adhesive faces.

INDUSTRIAL APPLICABILITY

The film dressing of the present invention possesses sufficient rigidity conferred by a carrier, and is easy to handle. Even with the carrier attached thereto, the film dressing of the present invention is capable of well fixing a wide variety of medical devices such as catheters to body surfaces, and offers good manipulability in separating the carrier.

Furthermore, because the film dressing of the present invention allows the release liner to be released partially, the release liner partially remains even after the adhesive face is exposed, and the remaining liner serves as a holding margin to ensure good workability for the operation of application.

The invention claimed is:

1. A film dressing comprising:
   a film dressing body having a film and an adhesive layer provided on one face of the film;
   a release liner covering an adhesive face of the adhesive layer and releasably laminated thereon;
   a carrier covering the other face of the film and releasably laminated thereon, wherein the carrier has a carrier-dividing portion that divides the outer shape thereof, whereby the carrier is divided into a carrier first portion and a carrier second portion, and
   a flap layer that covers the carrier-dividing portion is further laminated on the carrier, and the flap layer has a flap layer-dividing portion that divides an outer shape thereof, whereby the flap layer is divided into a flap layer first portion and a flap layer second portion,
   wherein
   the flap layer has a loop hardness of 15 to 60 mN,
   a partial region of the flap layer first portion is joined to the carrier first portion so as to leave a holding margin, and a partial region of the flap layer second portion is joined to the carrier second portion so as to leave a holding margin,
   the flap layer first portion and the flap layer second portion are in contact with each other at the flap layer-dividing portion,
   the flap layer first portion is joined to the carrier first portion in a region in the vicinity of the carrier-dividing portion, and the flap layer second portion is joined to the carrier second portion in a region in the vicinity of the carrier-dividing portion, and
   each distance from an end face of the carrier-dividing portion to a bonding portion of the flap layer first portion and to a bonding portion of the flap layer second portion is 1 mm-5 mm.

2. The film dressing of claim 1, wherein the carrier-dividing portion is linear, the carrier first portion and the carrier second portion are in contact with each other at the carrier-dividing portion, or the carrier-dividing portion is band-shaped, and the carrier first portion and the carrier second portion are apart from each other with the carrier-dividing portion sandwiched therebetween.

3. The film dressing of claim 1, wherein
   the carrier-dividing portion is band-shaped,
   the carrier first portion and the carrier second portion are apart from each other with the carrier-dividing portion sandwiched therebetween,
   in the band-shaped carrier-dividing portion, a filling layer having approximately the same width and thickness as those of the carrier-dividing portion is releasably inserted from the other face of the film, the filling layer having a dividing portion along the orientation of the carrier-dividing portion, whereby the filling layer is divided into a filling layer first portion and a filling layer second portion,
   the flap layer first portion is bonded straddlingly to the filling layer first portion and the carrier first portion, and the flap layer second portion is bonded straddlingly to the filling layer second portion and the carrier second portion.

4. The film dressing of claim 1, wherein the running direction of the flap layer-dividing portion is approximately the same as the running direction of the carrier-dividing portion.

5. The film dressing of claim 1, wherein the flap layer is a layer made of a flexible film or a layer made of a flexible unwoven fabric.

6. The film dressing of claim 1, wherein the release liner comprises one or more linear release liner-dividing portions that divide the outer shape of the release liner.

7. The film dressing of claim 6, wherein the release liner comprises two release liner-dividing portions in which running directions thereof are approximately the same as each other.

8. The film dressing of claim 6, wherein the running direction of the release liner-dividing portions is approximately the same as the running direction of the carrier-dividing portion.

* * * * *